US006630104B1

(12) United States Patent
Bayer (10) Patent No.: US 6,630,104 B1
(45) Date of Patent: *Oct. 7, 2003

(54) METHOD FOR STERILIZING AN ARTICLE (75) Inventor: Robert T. Bayer, Asheville, NC (US)

(73) Assignee: Cardinal Health 200, Inc., Dublin, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/441,421

(22) Filed: Nov. 16, 1999

(51) Int. Cl.⁷ .................................................. A61L 2/00
(52) U.S. Cl. ................. 422/1; 422/28; 422/40; 53/425; 53/466; 53/467
(58) Field of Search ................. 422/1, 28, 40; 53/425, 466, 467

(56) References Cited

U.S. PATENT DOCUMENTS

| | | | |
|---|---|---|---|
| 3,761,013 A | 9/1973 | Schuster | 206/439 |
| 3,780,857 A | 12/1973 | Rosano, Jr et al. | 206/370 |
| 4,196,245 A | 4/1980 | Kitson et al. | 428/198 |
| 4,201,031 A | 5/1980 | Wiles | 53/459 |
| 4,342,392 A | 8/1982 | Cox | 206/438 |
| 4,523,679 A * | 6/1985 | Paikoff et al. | 206/370 |
| 4,581,874 A | 4/1986 | Rechtsteiner et al. | 53/459 |
| 4,644,586 A | 2/1987 | Padgett | 383/102 |
| 4,644,732 A | 2/1987 | Morton | 383/121 |
| 4,863,785 A | 9/1989 | Berman et al. | 428/218 |
| 5,037,417 A * | 8/1991 | Ternstrom et al. | 609/385.2 |
| 5,072,832 A | 12/1991 | Valentine et al. | 206/570 |
| 5,325,987 A * | 7/1994 | Alpern et al. | 220/409 |
| 5,392,590 A * | 2/1995 | Ambrose et al. | 53/425 |
| 5,447,230 A * | 9/1995 | Gerondale | 206/363 |
| 5,635,134 A * | 6/1997 | Bourne et al. | 422/26 |
| 5,638,661 A * | 6/1997 | Banks | 53/469 |
| 5,673,541 A | 10/1997 | Arzuman et al. | 53/459 |
| 5,688,476 A | 11/1997 | Bourne et al. | 422/294 |
| 5,879,620 A | 3/1999 | Cohen | 206/439 |
| 6,406,764 B2 * | 6/2002 | Bayer | 428/35.2 |
| 2001/0036519 A1 * | 11/2001 | Bayer | 428/35.2 |

* cited by examiner

*Primary Examiner*—Krisanne Thornton
(74) *Attorney, Agent, or Firm*—Carter Schnedler & Monteith (57) ABSTRACT

There is provided an improved two-ply sterilization wrap and a method for using the improved sterilization wrap to sterilize an article. The wrap is made of a single sheet of sterilization material. The sheet is folded forming at least one fold. The folded sheet forms first and second overlapping panels and two layers of sterilization material. Preferably, the panels are bonded to each other. The folded single sheet provides two layers of sterilization material covering the article to be sterilized.

19 Claims, 4 Drawing Sheets

METHOD FOR STERILIZING AN ARTICLE

BACKGROUND OF THE INVENTION

This invention relates to sterilizing articles utilizing sterilization wrap. More particularly, it relates to sterilization wrap having two plies of sterilization material.

Reusable medical instruments must be sterilized prior to each use. Normally, these instruments are sterilized by steam or ethylene-oxide. In order for the instruments to remain sterile after the sterilization procedure, the instruments must be wrapped in a material called "sterilization wrap".

The most common type of sterilization wrap is a three-ply laminate consisting of a layer of melt blown polypropylene sandwiched between two layers of spun bond polypropylene. The wrap includes bond points all across the face of the material so that the material is held together, i.e., laminated. This three-ply material is commonly referred to as "SMS", which is short for spun bond—melt blown—spun bond. Most hospitals specify SMS as the sterilization wrap to be used because SMS is sufficiently porous to permit steam and ethylene-oxide to penetrate through the material to the surgical instruments, but has filtration properties sufficient to prevent the passage of most pathogens therethrough.

In most hospitals, there is a protocol which requires surgical instruments to be wrapped with two separate sheets of SMS so that in the event one sheet becomes torn, there is a redundancy which will maintain the sterility of the surgical instruments. The wrapping of surgical instruments with two separate sheets of sterilization wrap obviously is labor intensive in that the nurse must first place the instruments on one sheet of sterilization material and wrap the instruments, and then place the wrapped package on another sheet of sterilization material and wrap the instruments again.

In an attempt to reduce the labor required to provide dual wrapping of surgical instruments, Kimberly-Clark Corporation has developed a product called "One Step Sterilization Wrap". One Step Sterilization Wrap is made by bonding two separate sheets of sterilization wrap together. The Kimberly-Clark One Step product is described in U.S. Pat. Nos. 5,635,134 and 5,688,476. However, because the One Step wrap requires separate sheets to be bonded together, manufacturing costs are substantially increased. In addition, it requires precise alignment of the two separate movable sheets during the bonding process.

Thus there is a need for a sterilization wrap which provides two layers of protection, yet is inexpensive to manufacture and is easy to use.

OBJECTS OF THE INVENTION

It is therefore one object of this invention to provide an improved two-ply sterilization wrap.

It is another object of this invention to provide a two-ply sterilization wrap which is inexpensive to manufacture and is easy to use.

It is still another object of this invention to provide an improved method for sterilizing an article utilizing an improved two-ply sterilization wrap.

SUMMARY OF THE INVENTION

In accordance with one form of this invention, there is provided a sterilization wrap made from a single sheet of sterilization material. The sheet has first, second, third and fourth edges. The sheet is folded in half forming first and second overlapping panels and two layers of sterilization material. The fold runs from the third edge to the fourth edge. Because of the fold, the first edge is adjacent to the second edge and thus two layers of sterilization material are provided for an article to be sterilized by using a single sheet of sterilization material. The two panels may be affixed together along the first and second edges.

In addition, the third edge includes first and second portions and the fourth edge also includes first and second portions. The first panel may be also affixed to the second panel by bonding the first portion of the third edge to the second portion of the third edge, and by bonding the first portion of the fourth edge to the second portion of the third edge. In addition, the two panels may be affixed together by bonding adjacent to the fold.

In accordance with another form of this invention, there is provided a two-ply sterilization wrap made from a single sheet of sterilization material. The sheet is folded in half forming first and second overlapping equally sized panels. Each panel has edges. The first panel is bonded to the second panel so that the edges of the first panel remain adjacent to the edges of the second panel.

In accordance with another form of this invention, there is provided a two-ply sterilization wrap made from a single sheet of sterilization material. The sheet includes two folds. The sheet includes first, second, third and fourth edges. The first edge is adjacent to the second edge, and the third and fourth edges are opposite from one another. The folded sheet forms two adjacent equally sized panels. The first and second edges form an overlapping region. The first and second edges are bonded together along the overlapping region. The third edge includes first and second adjacent portions, and the fourth edge includes first and second adjacent portions. The first portion of the third edge may be bonded to the second portion of the third edge, and the first portion of the fourth edge may be bonded to the second portion of the fourth edge.

In accordance with another form of this invention, there is provided a method for sterilizing an article, including the steps of providing an article, wrapping the articles with sterilization wrap which is formed in accordance with one or more of the above described designs, and applying sterilization conditions to the wrapped article.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

DESCRIPTION OF THE PREFERRED EMBODIMENTS

Figure 1:
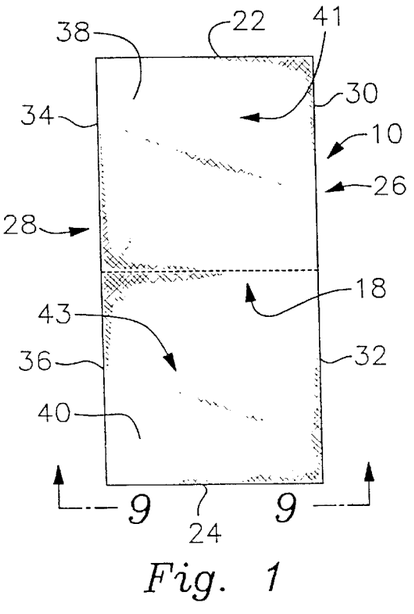
FIG. 1 is a plan view of the sterilization wrap in accordance with this invention, but prior to being folded.
Figure 9:
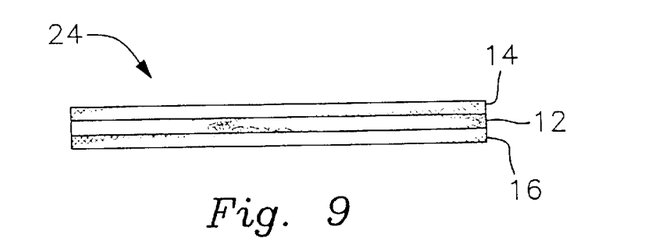
FIG. 9 is a side elevational view of the embodiment of FIG. 1 viewed from Lines 9—9.
Figure 10:
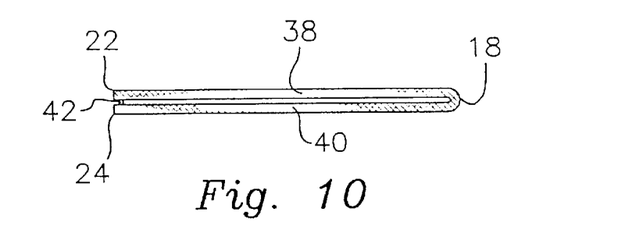
FIG. 10 is a right side elevational view of the embodiment of FIG. 2.
Figure 11:
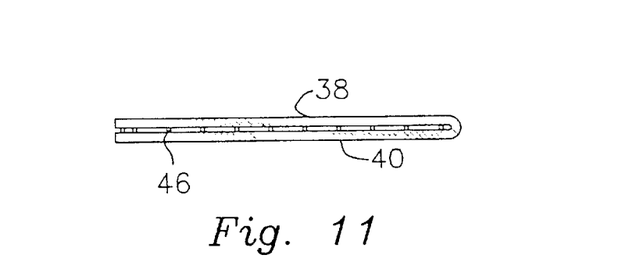
FIG. 11 is a right side elevational view of the embodiment of FIG. 4.

Referring now more particularly to FIG. 1, there is provided single sheet 10 which is made of sterilization material, which is preferably a three-ply laminate having a layer of melt blown polypropylene sandwiched between two layers of spun bonded polypropylene, referred to as SMS. A side elevational view showing the melt blown layer 12 sandwiched between spun bonded layers 14 and 16 is shown in FIG. 9. The layers 12, 14 and 16 are laminated or fixed together by a series of closely spaced small bond points consisting of ultrasonic welds. For simplicity, so as not to be confused with other bond points which are used for different purposes describe below, these SMS bond points are not shown. SMS is commercially available from Kimberly-Clark Corporation.

Sheet 10 includes first edge 22, second edge 24, third edge 26 and fourth edge 28. Third edge 26 includes a first portion 30 and a second portion 32, which are equal in length, and fourth edge 28 includes a first portion 34 and a second portion 36, which are also equal in length.

Figure 2:
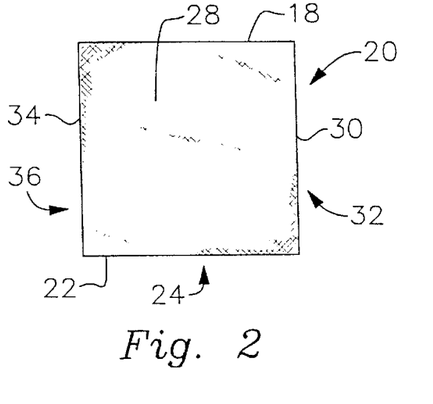
FIG. 2 is a plan view of the sterilization wrap of FIG. 1, but after having been folded, in accordance with this subject invention.

The single sheet of sterilization material 10 is folded in half along the fold line indicated by dotted line 18 from third edge 26 to fourth edge 28. The resulting folded article becomes two-ply sterilization wrap 20, as indicated in FIG. 2. Sterilization wrap 20 includes two equally sized panels 38 and 40 having first edge 22 which is aligned with and is adjacent to edge 24. First portion 30 of edge 26 is aligned with and is adjacent to second portion 32 of edge 26. First portion 34 of edge 28 is aligned with and is adjacent to second portion 36 of edge 28. As shown in FIG. 2, a single sheet two-ply sterilization wrap has been formed by simply folding an elongated sheet of sterilization material in half. However, it is preferred that the two panels 38 and 40 be bonded together. The preferred method of bonding is ultrasonic bonding which will result in bond points. Alternatively, hot melt glue, heated knife or wire, laser, water jet, or mechanical embossing may be used. Preferably, the central portions 41 and 43 of panels 38 and 40 are not bonded together.

When the phrase "edges are bonded together" is used herein, it should be understood that the bonding may occur on the material adjacent to the edges, or on the edges themselves.

Figure 3:
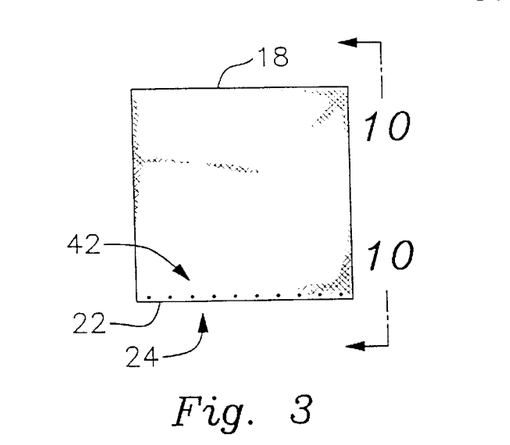
FIG. 3 is another embodiment of the invention shown in FIG. 2.

In one embodiment, shown in FIG. 3, the sheets are bonded together by a plurality of bond points 42 which are formed by ultrasonic bonding using a known procedure. These bond points 42 are provided along edges 22 and 24 so that the panels 38 and 40 are bonded together only along edges 22 and 24.

Figure 4:
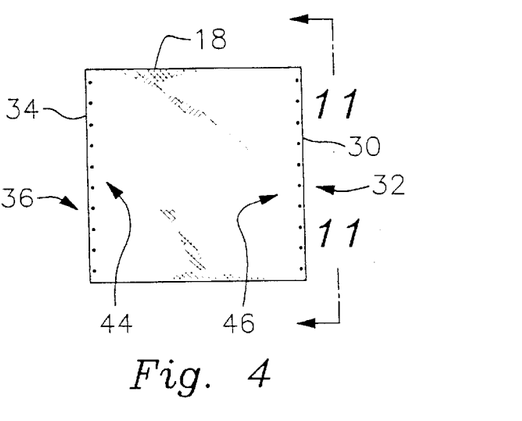
FIG. 4 is an alternative embodiment of that shown in FIG. 2.

FIG. 4 shows an alternative embodiment, which includes a plurality of bond points 44, which are provided along first portion 34,of edge 28 and second portion 36 of edge 28, and a plurality of bond points 46, which are provided along first portion 30 of edge 26 and second portion 32 of edge 26.

Figure 4A:
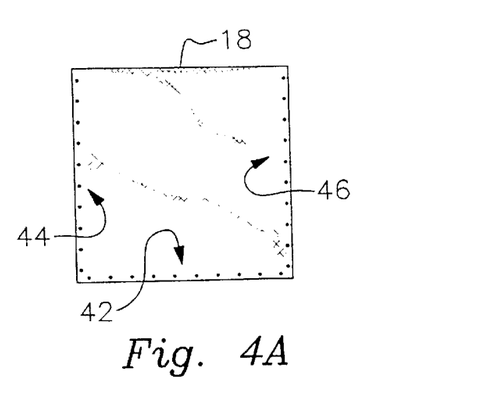
FIG. 4A is an alternative embodiment of that shown in FIG. 2.

FIG. 4A shows an alternative embodiment, which includes the bond points 44 and 46, and also includes bond points 42 along edges 22 and 24, i.e., a combination of the embodiments of FIGS. 3 and 4.

Figure 5:
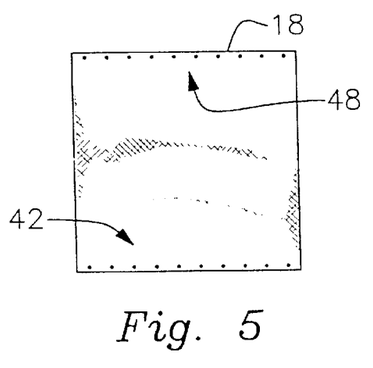
FIG. 5 is an alternative embodiment of that shown in FIG. 2.

FIG. 5 shows a modified version of the embodiment of FIG. 3, whereby a plurality of bond points 48 are provided by bonding along the fold line 18 so that the two panels 38 and 40 will stay together along fold line 18.

Figure 6:
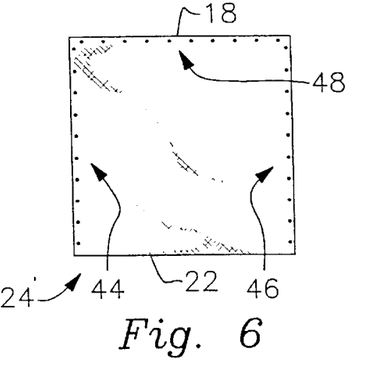
FIG. 6 is an alternative embodiment of that shown in FIG. 2.

FIG. 6 shows another alternative embodiment to that of FIG. 4, which also includes bond points 48 along fold line 18, as well as bond points 44 and 46 described above, but omits the bond points along edges 22 and 24.

Figure 7:
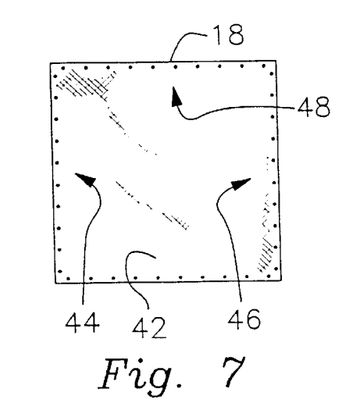
FIG. 7 is an alternative embodiment of that shown in FIG. 2.

FIG. 7 shows yet another alternative embodiment which includes bond points 42, 44, 46 and 48 on all of the edges and the fold of the two-ply sterilization wrap.

Figure 8:
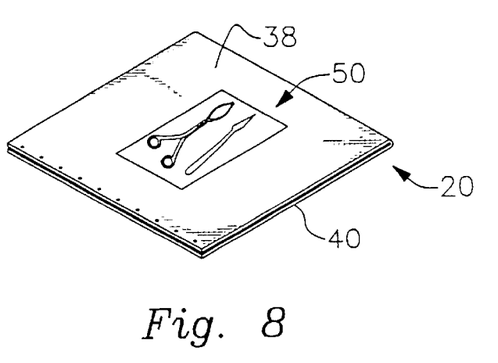
FIG. 8 is a perspective view of the embodiment of FIG. 3 having materials to be sterilized in preparation for wrapping.

FIG. 8 shows the single sheet two-ply sterilization wrap embodiment of FIG. 3 having articles 50 to be sterilized placed thereon in preparation for wrapping. Article 50 is wrapped by sterilization wrap 20 in a known fashion. Tape is placed over the wrapped article and the wrapped articles 50 are subjected to sterilization conditions, such as steam or ethylene-oxide. The other embodiments of the invention described herein may also be used to wrap article 50 for sterilization.

Figure 12:
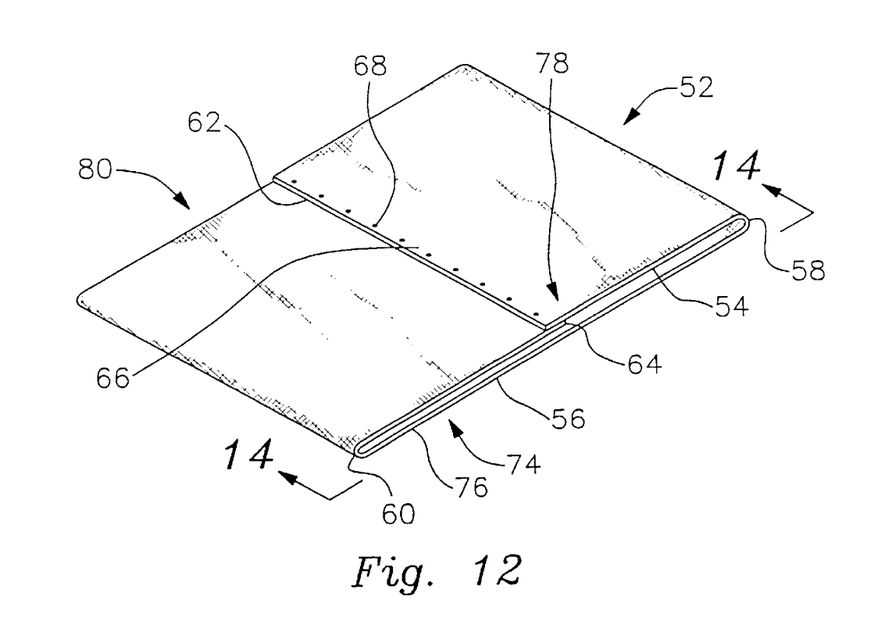
FIG. 12 is a perspective view of an alternative embodiment of the invention.
Figure 13:
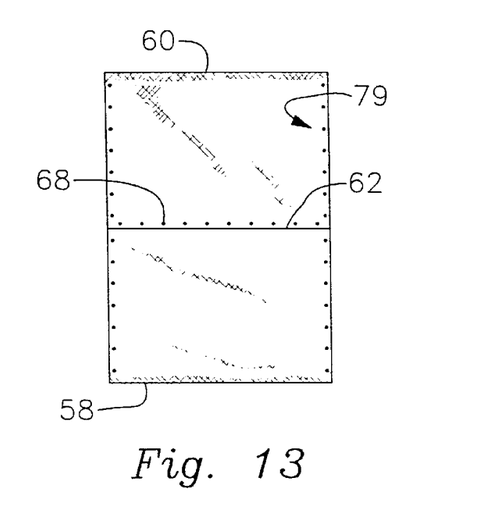
FIG. 13 is a plan view of an alternative embodiment of FIG. 12.
Figure 14:
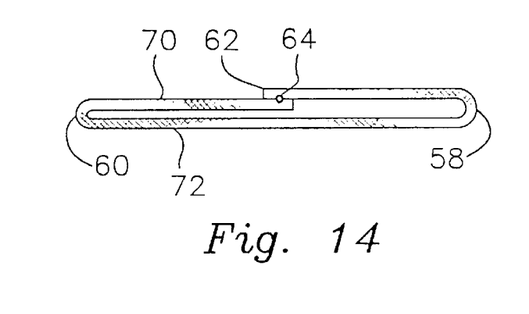
FIG. 14 is a side elevational view of the embodiment of FIG. 12 viewed from Lines 14—14.

FIGS. 12 through 14 show still another embodiment of the invention. Sterilization wrap 52 includes two plies 54 and 56, which is preferably made from the SMS sterilization material shown in FIG. 9. The sterilization wrap 52 is also made of a single sheet of sterilization material, but has been folded twice, namely, at folds 58 and 60 so that edge 62 overlaps edge 64 forming an overlap zone 66. The edges 62 and 64 are bonded together along overlap zone 66, preferably by ultrasonic bonding, resulting in bond points 68. The two folds 58 and 60 form first panel 70 and second panel 72, which are equal in size and which completely overlap one another. The third edge 74 of the single sheet includes first portion 76 and second portion 78. First portion 76 and second portion 78 of third edge 74 are adjacent to one another. As shown in FIG. 13, the first portion 76 of edge 74 and the second portion 78 of edge 74 may be bonded together, again, by using ultrasonic bonding, thereby forming bond points 79. Likewise, the first and second portions of the fourth edge 80 may also be bonded together in an identical fashion.

Figure 15:
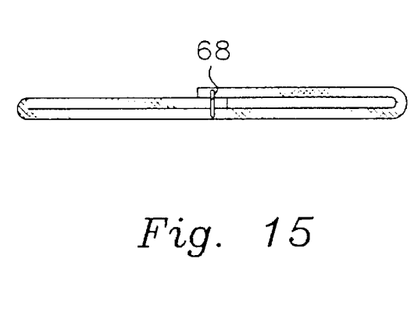
FIG. 15 is an alternative embodiment of that shown in FIG. 14.

As shown in FIG. 15, the bond points 68 may also provide bonding between panels 70 and 72. That is, the bond 68 may go all the way through to panel 72, which will help stabilize the sterilization wrap.

Figure 16:
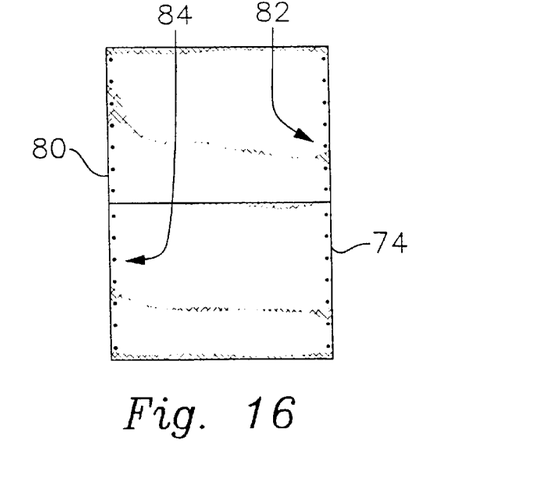
FIG. 16 is an alternative embodiment of that shown in FIG. 12.

FIG. 16 shows still another embodiment of the invention, which is similar to that shown in FIG. 13, except that the article is only bonded along the third edge 74 and the fourth edge 80, as shown by bond points 82 and 84, i.e., there is no bonding along the overlap of edges 62 and 64. Alternatively, the embodiments of FIGS. 12 and 16 could be combined, as shown in FIG. 13, so that the overlap of edges 62 and 64 are bonded as well as edges 74 and 80. By using the embodiments shown in FIGS. 4A, 7 and 13, there are no loose, i.e., unsealed, edges. By sealing all edges, the fiber and particle generation often associated with untreated edges of SMS is reduced.

The sterilization wrap assembly of the subject invention is easy to manufacture in that it is simply cut into the rectangular shape shown in FIG. 1 and folded into two equal sized panels in the shape shown in FIG. 2. Once the sheet 10 is cut, only a single sheet is used during the manufacturing of the sterilization wrap. Preferably, the two panels are bonded together by ultrasonic welding, which is commonly used to manufacture SMS. Thus there is no need for the nurse to handle two separate sheets of sterilization wrap, nor is there a need for the manufacturer to handle two separate sheets of sterilization wrap and bond the two separate sheets together.

From the foregoing description of the preferred embodiments of the invention, it will be apparent that many modifications may be made therein. It will be understood, however, that the embodiments of the invention are an exemplification of the invention only and that the invention is not limited thereto. It is to be understood, therefore, that it is intended in the appended claims to cover all modifications as fall within the true spirit and scope of the invention.

I claim:

1. A method for sterilizing an article using sterilization material which includes a single sheet of sterilization material; said sheet having first, second, third and fourth edges; said sheet being folded in half, wherein a fold from said third edge to said fourth edge is formed;
   first and second overlapping panels forming two layers of sterilization material; said first edge is adjacent to said second edge; said first panel having an outer surface facing away from said second panel comprising the steps of:
   providing an article;
   placing said article on the outer surface of the first panel;
   wrapping the article with the folded sheet of sterilization material;
   applying sterilization conditions to the wrapped article, whereby two layers of sterilization material are provided for an article to be sterilized by using a single sheet of sterilization material.

2. A method as set forth in claim 1, wherein said first panel is affixed to said second panel by bonding said first edge to said second edge.

3. A method as set forth in claim 1, wherein said third edge has first and second portions; said fourth edge has first and second portions; said first panel affixed to said second panel by bonding said first portion of said third edge to said second portion of said third edge, and by bonding said first portion of said fourth edge to said second portion of said fourth edge.

4. A method as set forth in claim 1, wherein said first edge is bonded to said second edge; said third edge having first and second portions; said fourth edge having first and second portions; said first portion of said third panel is bonded to said second portion of said third panel, and said first portion of said fourth panel is bonded to said second portion of said fourth panel.

5. A method as set forth in claim 2, wherein said first panel is affixed to said second panel by bonding said panels adjacent to said fold.

6. A method as set forth in claim 5, wherein said third edge has first and second portions; said fourth edge has first and second portions; said first portion of said third edge is bonded to said second portion of said third edge, and said first portion of said fourth edge is bonded to said second portion of said fourth edge.

7. A method as set forth in claim 3, wherein said first panel is affixed to said second panel by bonding said panels adjacent to said fold.

8. Method as set forth in claim 1, wherein said sterilization material is a three-ply composite of spun bond, melt blown, spun bond polypropylene.

9. A method for sterilizing an article using sterilization material which includes a single sheet of sterilization material; said sheet being folded in half, thereby forming first and second overlapping equally sized panels; each panel having edges; said first panel being bonded to said second panel, whereby the edges of said first panel are adjacent to the edges of said second panel; said first panel having an outer surface facing away from said second panel comprising the steps of:
   providing an article;
   placing the article on the outer surface of the first panel;
   wrapping the article with the folded sheet of sterilization material;
   applying sterilization conditions to the wrapped article.

10. A method as set forth in claim 9, wherein each panel has first, second and third edges; said sheet having a fold; said first edge of each panel being opposite to said fold; said first edge of said first panel bonded to said first edge of said second panel.

11. A method asset forth in claim 9, wherein said sheet having first, second, third and fourth edges and a fold; said first and second edges being opposite to said fold; said third edge including first and second portions; said first portion of said third edge being bonded to said second portion of said third edge; said fourth edge including first and second portions; said first portion of said fourth edge being bonded to said second portion of said fourth edge.

12. A method as set forth in claim 10, wherein said panels are bonded along said fold.

13. A method as set forth in claim 11, wherein said panels are bonded along said fold.

14. A method as set forth in claim 9, wherein said material is a three-ply composite of spun bond, melt blown, spun bond polypropylene.

15. A method as set forth in claim 9, wherein said panels are bonded only along at least portions of adjacent edges, whereby central portions of said panels are not bonded.

16. A method for sterilizing an article using sterilization material which includes a single sheet of sterilization material; said sheet having first, second, third and fourth edges; said sheet being folded in half, wherein a fold from said third edge to said fourth edge is formed;
   first and second overlapping panels forming two layers of sterilization material; said first edge is adjacent to said second edge; said panels being bonded together; said first panel having an outer surface facing away from said second panel comprising the steps of:
   providing an article;
   placing the article on the outer surface of said first panel;
   wrapping the article with the folded sheet of sterilization material;
   applying sterilization conditions to the wrapped article, wherein two layers of.sterilization material are provided for the article to be sterilized using a single sheet of sterilization material.

17. A method for sterilizing an article using sterilization material which includes a single sheet of sterilization material; said sheet having two folds forming first and second overlapping equally sized panels; said first panel having an outer surface facing away from said second panel; said sheet having first and second edges; said first edge overlapping said second edge forming an overlapping zone; said first edge being bonded to said second edge within said overlapping zone comprising the steps of:

provi­ding an article;

placing the article on the outer surface of the first panel;

wrapping the article with the folded sheet of sterilization material;

applying sterilization conditions to the wrapped article.

18. A method as set forth in claim 17, wherein said sheet having third and fourth edges; said third edge including first and second portions; said first portion of said third edge being bonded to said second portion of said third edge; said fourth edge including first and second portions; said first portion of said fourth edge being bonded to said second portion of said fourth edge.

19. A method for sterilizing an article comprising:

providing an article;

wrapping the article with sterilization material which comprises:

a single sheet of sterilization material; said single sheet including at least one fold forming first and second panels; said first panel being contiguous with said second panel; said sheet including first and second portions; said first portion being bonded to said second portion so that said first panel will remain contiguous with said second panel.

* * * * *

UNITED STATES PATENT AND TRADEMARK OFFICE
CERTIFICATE OF CORRECTION

| | | |
|---|---|---|
| PATENT NO. | : 6,630,104 B1 | Page 1 of 1 |
| APPLICATION NO. | : 09/441421 | |
| DATED | : October 7, 2003 | |
| INVENTOR(S) | : Robert T. Bayer | |

It is certified that error appears in the above-identified patent and that said Letters Patent is hereby corrected as shown below:

On the cover page, the following is added:

RELATED U.S. APPLICATION DATA (62) Divisional of Serial No. 09/080,707 filed May 18, 1998, now U.S. Pat. 6,406,764

In Column 1, prior to line 4, Background of the Invention, the following is added:

This is a divisional of Serial No. 09/080,707 filed May 18, 1998, now U.S. Pat. 6,406,764.

Signed and Sealed this

Tenth Day of April, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,630,104 B1 | Page 1 of 1 |
| APPLICATION NO. | : 09/441421 | |
| DATED | : October 7, 2003 | |
| INVENTOR(S) | : Robert T. Bayer | |

It is certified that error appears in the above-identified patent and that said Letters Patent is hereby corrected as shown below:

On the cover page, the following is added:

RELATED U.S. APPLICATION DATA (62) Divisional of Serial No. 09/080,707 filed May 18, 1998, now U.S. Pat. 6,406,764

In Column 1, prior to line 4, Background of the Invention, the following is added:

This is a divisional of Serial No. 09/080,707 filed May 18, 1998, now U.S. Pat. 6,406,764.

Signed and Sealed this

First Day of May, 2007

JON W. DUDAS
*Director of the United States Patent and Trademark Office*